United States Patent [19]

Viera

[11] Patent Number: 5,497,785
[45] Date of Patent: Mar. 12, 1996

[54] CATHETER ADVANCING GUIDEWIRE AND METHOD FOR MAKING SAME

[75] Inventor: Fernando M. Viera, Hialeah, Fla.

[73] Assignee: Cordis Corporation, Miami Lakes, Fla.

[21] Appl. No.: 281,444

[22] Filed: Jul. 27, 1994

[51] Int. Cl.⁶ .................................................. A61M 25/01
[52] U.S. Cl. ............................................ 128/772; 128/657
[58] Field of Search .................................... 128/657, 772; 604/164, 170, 280, 282

[56] References Cited

U.S. PATENT DOCUMENTS

| | | | |
|---|---|---|---|
| 3,906,938 | 9/1975 | Fleischhacker | 128/772 |
| 3,973,556 | 8/1976 | Fleischhacker et al. | 128/2 M |
| 4,079,757 | 3/1978 | Fischer et al. | 138/121 |
| 4,554,929 | 11/1985 | Samson et al. | 128/657 X |
| 4,676,249 | 6/1987 | Arenas et al. | 128/657 |
| 4,846,186 | 7/1989 | Box et al. | 128/657 |
| 4,947,425 | 8/1990 | Grizmala et al. | 379/410 |
| 4,955,862 | 9/1990 | Sepetka | 604/164 |
| 5,001,825 | 3/1991 | Halpern | 29/456 |
| 5,004,456 | 4/1991 | Botterbusch et al. | 604/53 |
| 5,095,915 | 3/1992 | Engelson | 128/772 |
| 5,102,403 | 4/1992 | Alt | 604/280 |
| 5,109,830 | 5/1992 | Cho | 128/772 X |
| 5,170,787 | 12/1992 | Lindegren | 128/772 X |
| 5,171,383 | 12/1992 | Sagaye et al. | 148/564 |
| 5,195,989 | 3/1993 | Euteneuer | 604/280 |
| 5,213,111 | 5/1993 | Cook et al. | 128/772 |
| 5,228,453 | 7/1993 | Sepetka | 128/772 |
| 5,251,640 | 10/1993 | Osborne | 128/772 |

FOREIGN PATENT DOCUMENTS

| | | | |
|---|---|---|---|
| 0377453 | 7/1990 | European Pat. Off. | 128/772 |
| 03770453-A | 11/1990 | European Pat. Off. | |
| 92/014508 | 9/1992 | WIPO | 128/772 |

OTHER PUBLICATIONS

Cordis® Brochure, "Discover the Benefits of a Sleek Physique", Mar. 1993.

*Primary Examiner*—Sam Rimell
*Attorney, Agent, or Firm*—Allen, Dyer, Doppelt, Franjola & Milbrath

[57] ABSTRACT

A guidewire includes an elongate flexible unitary body with a plurality of spaced apart grooves in its outer surface and defining a tip support section. In one embodiment, the plurality of grooves take the form of a series of equally axially spaced apart transverse grooves which extend circumferentially around the outer surface of the elongate flexible body. A cross section of each groove may have a V-shape or U-shape, with each groove having rounded over opposing outer edges. A distal tip section is connected to the tip support section, and a main section is connected to the tip support section opposite the distal tip section. Preferably the main section, tip support section, and a portion of the distal tip section are formed of a unitary metal body or wire. The distal tip section also preferably includes a flattened wire portion surrounding by a wound coil.

32 Claims, 2 Drawing Sheets

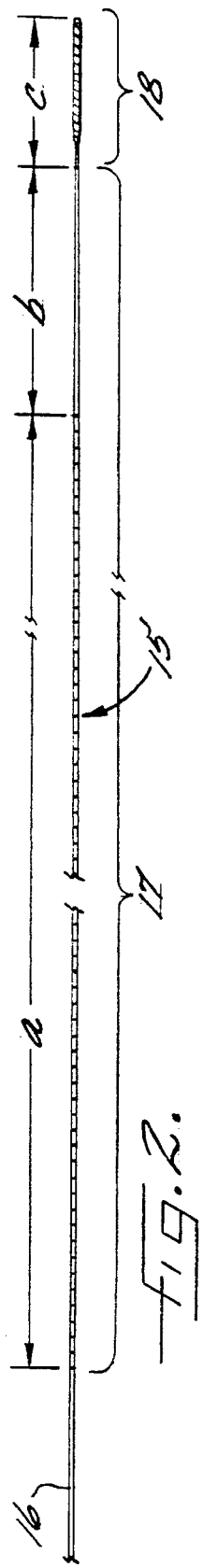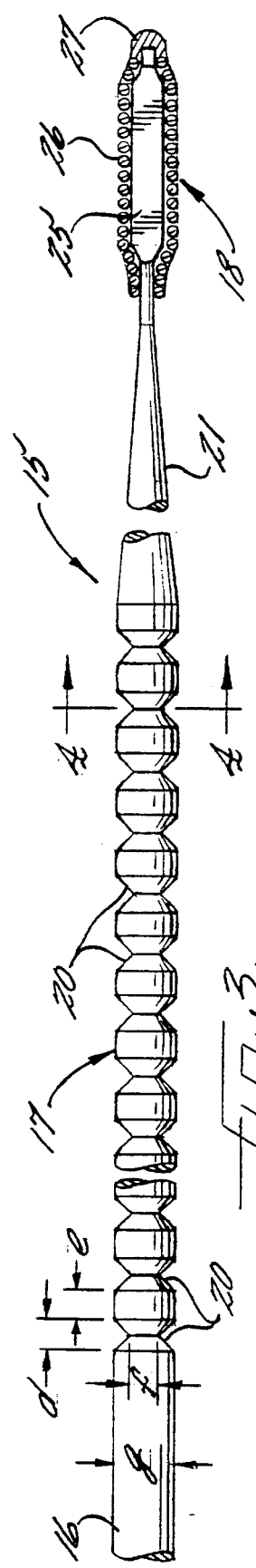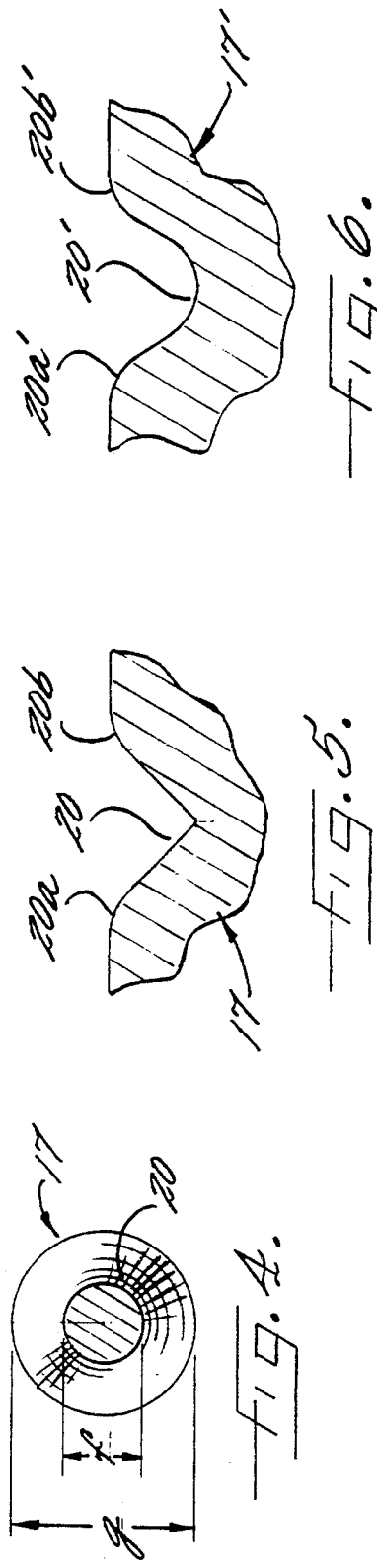

CATHETER ADVANCING GUIDEWIRE AND METHOD FOR MAKING SAME

FIELD OF THE INVENTION

This invention relates to the field of medical devices, and more particularly, to a flexible guidewire for placing a catheter within a patient's body.

BACKGROUND OF THE INVENTION

A catheter is commonly used to access an internal body site for either diagnostic or therapeutic purposes. For example, in percutaneous coronary angioplasty, a catheter having a deflated balloon at its distal end is guided through a patient's cardiovascular system to a desired target position within a diseased coronary artery. When in place, the balloon is inflated to compress deposits that have accumulated along the inner walls of the coronary artery. The interior passageway of the artery is thus widened, and blood flow to the heart is increased.

A catheter typically uses a guidewire to aid in placing the catheter at the target site within a blood vessel. A guidewire is typically inserted into a lumen of a balloon catheter, for example, with a distal tip section of the guidewire extending beyond the end of the catheter. The distal tip of the guidewire may be bent at a predetermined angle to facilitate steering of the guidewire to a desired blood vessel at a branch point by selectively rotating a proximal end of the guidewire while viewing the distal tip section by fluoroscopy. The guidewire must be very flexible to navigate bends and turns within the blood vessel, particularly at a distal end portion adjacent the distal tip. The distal end portion of the guidewire may be required to make relatively sharp bends to reach the diseased portion of the coronary artery.

One type of catheter guidewire has a tapered diameter along its length to provide a reduced diameter distal end portion of greater flexibility. In some guidewires, a reduced diameter distal end portion may include a covering of a wound coil to increase the columnar strength and the torque transmitting ability of the guidewire to permit manipulation of the guidewire from the proximal end. See, for example, U.S. Pat. No. 4,676,249 entitled *Multi-Mode Guidewire* to Arenas et al.; U.S. Pat. No. 4,846,186 entitled *Flexible Guidewire to Box* et al.; and U.S. Pat. No. 5,001,825 entitled *Catheter Guidewire Fabrication Method* to Halpern; all of which are assigned to the assignee of the present invention.

U.S. Pat. No. 5,171,383 to Sagaye et al. entitled *Method of Manufacturing a Differentially Heat Treated Catheter Guide Wire,* discloses a catheter guidewire wherein flexibility is sequentially increased along a highly elastic wire by heat treatment. A thermoplastic resin or coil spring may be applied to the distal end.

Yet another guidewire is disclosed in U.S. Pat. No. 5,095,915 entitled *Guidewire with Flexible Distal Tip* to Engelson which discloses a guidewire including a wire core having a distal end portion encased in a polymer sleeve extending from the distal tip for a length in the range of from 3 to 25 cm. The polymer sleeve increases the columnar strength of the wire core while, in one embodiment, axially spaced grooves formed in the sleeve provide enhanced flexibility. The sleeve may be formed by extrusion or molding, and secured to the wire core by an adhesive, heat shrinking, or by chemical bonding. Alternately, the sleeve may be formed by dip coating the core wire tip. The grooves in the polymeric sleeve are preferably formed after attachment of the sleeve to the wire core, such as by using a type of lathe.

Unfortunately, many conventional guidewires are not suitable to advance heavier catheters within a blood vessel. For example, conventional guidewires may not be sufficiently flexible, yet resistant to buckling to facilitate placement of a laser, for example, along a tortuous path within a blood vessel. In addition, it may also be advantageous to avoid a guidewire having a polymeric coating and the like on a core wire, because the coating may tend to flake or otherwise separate from the underlying core wire, especially along a length of the guidewire that is repeatedly flexed.

SUMMARY OF THE INVENTION

It is therefore an object of the present invention to provide a catheter guidewire that is flexible, capable of transmitting torque, and resistant to kinking or buckling, especially when positioning relatively large catheters within a patient.

These and other objects, features and advantages according to the invention are provided by a guidewire including an elongate flexible body defining a longitudinally extending tip support section, and wherein the tip support section has a plurality of spaced apart grooves defined in an outer surface thereof. The tip support section enhances flexibility while resisting buckling to thereby facilitate placing the guidewire within a patient. The tip support section also permits torque transmission through the relatively flexible tip support section to further facilitate manipulation of the distal tip from the proximal end of the guidewire.

The tip support section preferably has a length in a range of about 5 to 15 inches, which is particularly suited for accessing areas within the coronary arteries. The distal tip section is preferably connected to the tip support section, and a main section is preferably connected to the tip support section opposite the distal tip. Each of the sections is preferably integrally formed from a metal wire.

The tip support section also preferably includes a tapered diameter portion extending longitudinally between the plurality of spaced apart grooves and the distal tip section. The distal tip section is preferably provided by a flattened portion of the metal wire and a wound coil surrounding the flattened portion so that the distal tip section is bendable and shape-retaining.

The plurality of spaced apart grooves preferably take the form of a series of equally axially spaced apart transverse grooves which extend circumferentially around the outer surface of the tip support section. The equally spaced circumferential grooves provide uniform flexibility for the tip support section.

The tip support section preferably has a circular cross-sectional shape in areas between adjacent transverse grooves of diameter equal to a predetermined outer diameter of the main section of the guidewire. Each groove, and each axial spacing between adjacent grooves, may range from about 0.01 to 0.10 inches, and more preferably about 0.02 to 0.10 inches. Accordingly, each groove may have a width defined in the axial direction, so that a ratio of the groove width to groove spacing is in a range of about 0.1 to 10. In addition, each of the grooves preferably has a predetermined depth defining an inner diameter which may range from about 0.006 to 0.010 inches. The outer diameter of the adjacent portion between grooves may have an outer diameter which ranges from about 0.010 to 0.038 inches.

Each groove may have a V-shaped or U-shaped cross-section to impart the desired relatively high flexibility while still retaining sufficient strength to resist buckling and permit transmission of torque through the guidewire. Moreover, each groove preferably has rounded over opposing outer edges, that is, those edges adjacent an imaginary cylinder defined by outer surface portions of the tip support section. The rounded over edges facilitate placement within a catheter and reduce the risk of snagging and/or damaging the catheter.

A method aspect of the present invention is for forming the flexible catheter guidewire and includes the steps of: providing an elongate flexible unitary body defining a tip support section of the guidewire; and forming a plurality of spaced apart grooves in an outer surface of the tip support section for enhancing flexibility while resisting buckling to thereby facilitate placing the guidewire within a patient. The opposing outer edges of each of the plurality of grooves are preferably rounded over.

The method also preferably includes the step of forming a tapered diameter section along the elongate flexible unitary body between the tip support section and the distal tip section. This tapered diameter portion further enhances flexibility while providing support for the distal tip section.

The method also preferably includes the step of forming a bendable, shape-retaining distal tip section adjacent the tip support section. The distal tip section may be formed by flattening a portion of the elongate flexible unitary body and covering same with a wound coil.

BRIEF DESCRIPTION OF THE DRAWINGS

FIG. 2 is a side elevational view of portions of the guidewire according to the invention.

FIG. 3 is an enlarged side elevational view of the guidewire as shown in FIG. 2 with a portion of the distal tip section shown in cross-section.

FIG. 4 is a greatly enlarged cross-sectional view taken along lines 4—4 of FIG. 3.

FIG. 5 is a greatly enlarged cross-sectional view of a V-shaped groove in the guidewire as shown in FIG. 3.

FIG. 6 is a greatly enlarged cross-sectional view of a U-shaped groove as in an alternative embodiment of the guidewire according to the invention.

DETAILED DESCRIPTION OF PREFERRED EMBODIMENTS

Figure 1:
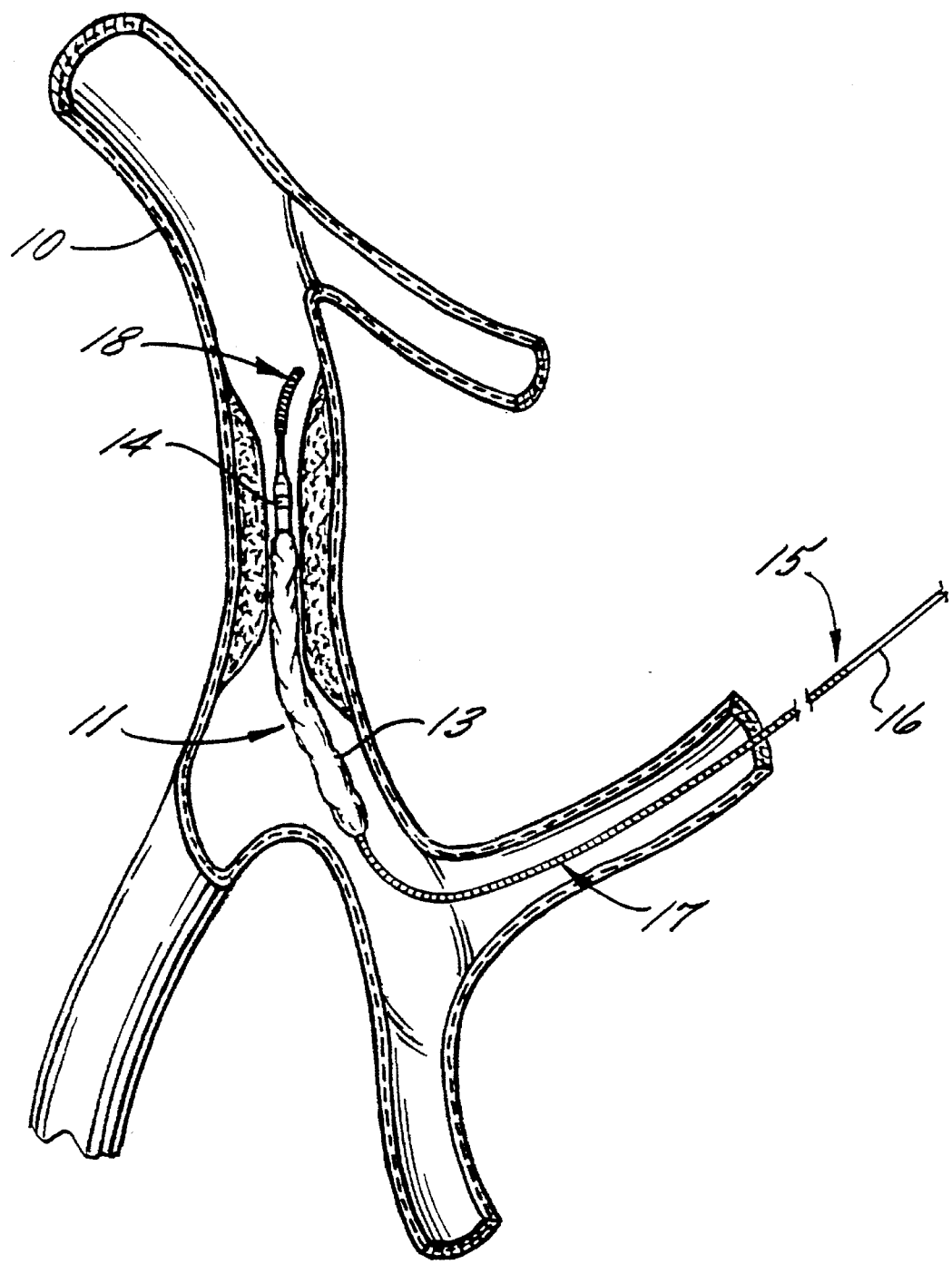
FIG. 1 is a schematic cross-sectional view illustrating a catheter inserted into an occluded blood vessel and with a tubular portion of the catheter removed for clarity in illustrating the guidewire according to the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout and prime notation is used to indicate similar elements in alternate embodiments.

Referring now to FIG. 1, an occluded blood vessel 10 with a catheter 11 inserted therein is shown. The catheter 11 is placed within the blood vessel 10, such as a coronary artery of the patient, using the guidewire 15 according to the invention. A balloon angioplasty catheter 11 is illustrated of the type which typically includes two or more lumens, one for the guidewire 15 and one to deliver air to inflate the balloon 13, for example. A radiopaque band 14 may also be used to locate the catheter 11 by fluoroscopy as the catheter is placed through the blood vessel of the patient. Those of skill in the art will readily recognize that other types of medical devices may also be positioned within a patient using the guidewire 15 according to the invention. For example, the guidewire 15 may also be used to place an optical fiber within a blood vessel to deliver laser light to remove an occlusion.

The guidewire 15 passes through the catheter 11 so that a distal tip section 18 extends beyond the end of the catheter and the balloon 13. The distal tip section 18 is formed to be bendable, yet shape-retaining, so that a slight curve may be formed therein. This curved portion may be rotated by manipulating a proximal end of the guidewire 15 to thereby steer the guidewire and catheter along a desired route as would be readily understood by those skilled in the art. In other words, a torque applied to the proximal end of the guidewire 15 is transmitted along the length of the guidewire to properly position the distal tip section 18 so that the guidewire may be advanced along a desired path within the patient.

Referring now additionally to FIGS. 2 through 5, the flexible guidewire 15 according to the invention is described in greater detail. The guidewire 15 is preferably formed of an elongate flexible unitary body having a longitudinally extending main section 16, a longitudinally extending tip support section 17 connected to the main section, and a distal tip section 18 connected to the tip support section. The total length of the guidewire 15 is preferably about 71 inches, such as for use with an angioplasty balloon catheter 11. The elongate flexible unitary body of the guidewire 15 is preferably a wire formed of a material, such a stainless steel, nickel, titanium or alloys of nickel, as would be readily understood by those skilled in the art.

The main section 16 of the guidewire 15 is preferably about 75–90% of the total length of the guidewire. The tip support section 17 preferably has an overall length (a+b) in a range of about 5 to 15 inches and, more preferably about 9.5 inches. As shown in the illustrated embodiment, the tip support section 17 also includes a tapered diameter portion 21 having a length b of about 2 inches between the tip support section 17 and the grooved portion a of the tip support section. The tapered portion 21 of the guidewire 15 provides enhanced flexibility and provides a smooth transition in diameter down to the diameter of the distal tip section 18. The distal tip section 18 is preferably about 0.25 to 1.5 inches in length c.

The tip support section 17 has a plurality of axially spaced apart circumferentially extending grooves 20 defined along a first length of an outer surface. The grooves 20 enhance flexibility of the tip support section 16 while resisting buckling to thereby facilitate insertion of the guidewire 15 along a tortuous path within a blood vessel of the patient. The tip support section 17 according to the invention also readily transmits torque to cause rotation and, thus, permit steering of the distal tip section 18. Moreover, since the grooves are formed directly in the outer surface of the unitary body, there is no coating or plastic material required which may flake or otherwise separate from an underlying core wire.

The guidewire's main section 16 preferably has a circular cross-sectional shape of a predetermined diameter which is the same as the diameter of the ring-like portions formed between adjacent grooves of the tip support section 17. The plurality of grooves 20 preferably take the form of a series equally axially spaced apart transverse grooves which extend circumferentially around the outer surface of the elongate flexible body as illustrated.

Other groove arrangements or groove means are contemplated by the present invention that provide enhanced flexibility compared to a portion of the flexible elongate body having a uniform diameter, for example. The illustrated equally spaced grooves 20 extending completely around the circumference provide substantially uniform flexibility for the tip support section 17. For example, if a gradually decreasing flexibility profile were desired, the spacing between adjacent grooves may gradually decrease in the direction toward the distal tip section 18. In addition, if a preferred bending direction were desired, the grooves may be formed to extend only part way around the outer surface of the elongate flexible unitary body or wire.

As shown in the greatly enlarged view of FIG. 3, each of the grooves 20 may have a V-shaped cross-section. As also shown, the outer edges 20a, 20b of each groove are preferably rounded over rather than sharp. The rounded over edges 20a, 20b facilitate positioning of the guidewire 15 within a lumen of a catheter and are less likely to abrade the catheter. In an alternative embodiment as shown in FIG. 6, the grooves 20' may have a U-shaped cross-section. The U-shaped grooves 20' also preferably have rounded over outer edges 20a', 20b'. Other cross-sectional shapes may also be used as would be readily appreciated by those skilled in the art.

Each groove 20 preferably has a width d in the axial direction in the range of about 0.01 to 0.10 inches, and more preferably about 0.02 to 0.10 inches. In addition, the spacing e between adjacent grooves is preferably in a range of about 0.01 to 0.10 inches and more preferably, about 0.02 to 0.10 inches. Accordingly, a ratio of the width d of each groove 20 to the spacing e between adjacent grooves is preferably in the range of about 0.1 to 10. For a typical guidewire 15 the width d may preferably be about 0.10 inches and the spacing e may be about 0.10 inches as well. In addition, as shown perhaps best in FIG. 4, the tip support section 17 has a circular cross-sectional shape in areas between adjacent grooves 20 with a predetermined diameter g which is also equal to the diameter of the main section 16. In other words, the areas between adjacent grooves 20 defines an imaginary cylinder having a predetermined diameter g. Each of the grooves 20 also has a depth defining an innermost diameter f in the range of about 0.006 to 0.01 inches. In addition, the outer diameter g of the portion between adjacent grooves 20 is preferably in a range of about 0.010 to 0.038 inches. For a typical guidewire 15 the outer diameter g may be 0.013 inches, and the inner diameter f of a groove may be 0.0072 inches.

As shown perhaps best in FIG. 3, the distal tip section 18 may be provided by a flattened portion of the flexible elongate unitary body or wire having a wound coil spring 26 covering the flattened portion. The flattened portion may be about 0.0012 inches thick. The distal tip section 18 is thus bendable and shape-retaining to permit the physician to set a predetermined curvature in the distal tip section 18 to enhance steerability within the blood vessel of the patient. The distal tip 27 of the wound coils may be welded to form a smooth surface for passage through the blood vessel of the patient as would be readily understood by those skilled in the art.

A method aspect of the present invention is for forming the flexible guidewire 15 as described above. The method includes the steps of: providing an elongate flexible unitary body defining a tip support section 17 of the guidewire; and forming a plurality of spaced apart grooves 20 in an outer surface of the tip support section for enhancing flexibility while resisting buckling to thereby facilitate placing the guidewire within a patient.

The grooves 20 may preferably be formed extending circumferentially around the outer surface of the tip support section and equally spaced along the axis of the guidewire 15 and wherein each spaced apart groove has a width such that a ratio of the width to the spacing between adjacent grooves is in a range of about 0.1 to 10. The grooves may be formed by the process of precision centerless grinding available as a service from Microguide Co. of Tehachare, Calif. 93561. The opposing outer edges 20a, 20b of each of the plurality of grooves is preferably rounded over.

The method also preferably includes the step of forming a bendable, shape-retaining distal tip section 18 adjacent the tip support section 17. The distal tip section may be formed by flattening a portion 25 of the elongate flexible unitary body and covering same with a wound coil 26.

The method also preferably includes the step of forming a tapered diameter section 21 along the elongate flexible unitary body between the grooved portion of the tip support section and the distal tip section 18. This tapered diameter portion further enhances flexibility while providing support for the distal tip section.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A flexible guidewire for use in placing a catheter within a patient, said guidewire comprising:

an elongated flexible unitary body defining a longitudinally extending tip support section, said tip support section having a plurality of axially spaced apart transverse grooves defined in an outer surface thereof for enhancing flexibility while resisting buckling to thereby facilitate placing the guidewire within a patient, said tip support section having a plurality of axially spaced apart longitudinally extending cylindrical outer surface portions between adjacent transverse grooves of constant and uniform circular cross-section and collectively defining an imaginary circular cylinder of constant and uniform diameter, each of said transverse grooves having a pair of opposing outer edges, adjacent respective cylindrical outer surface portions, being rounded over to thereby facilitate positioning of said tip support section within a catheter; and a distal tip section connected to said tip support section.

2. A guidewire according to claim 1 wherein said tip support section further comprises a tapered diameter portion extending longitudinally between said plurality of spaced apart grooves and said distal tip section.

3. A guidewire according to claim 1 wherein said guidewire further comprises a longitudinally extending main section connected to said tip support section opposite said distal tip section, wherein said main section has a circular cross-sectional shape of predetermined diameter, and wherein the imaginary cylinder defined by outer surface portions of said tip support section has a diameter equal to the predetermined diameter of said main section.

4. A guidewire according to claim 1 wherein said series of axially spaced apart transverse grooves are equally axially spaced apart transverse grooves which extend circumferentially around the outer surface of said tip support section.

5. A guidewire according to claim 4 wherein each axially spaced apart transverse groove has a width such that a ratio of the width to the axial spacing between adjacent grooves is in a range of about 0.1 to 10.

6. A guidewire according to claim 1 wherein each of said spaced apart transverse grooves has a V-shaped cross-section.

7. A guidewire according to claim 1 wherein each of said spaced apart transverse grooves has a U-shaped cross-section.

8. A guidewire according to claim 1 wherein said tip support section has a length in a range of about 5 to 15 inches.

9. A guidewire according to claim 1 wherein said elongate flexible unitary body is a metal wire; and wherein said distal tip section comprises a flattened portion of said metal wire and a wound coil surrounding said flattened portion so that said distal tip section is bendable and shape-retaining.

10. A flexible guidewire for use in placing a catheter within a patient, said guidewire comprising:

an elongate flexible body defining a longitudinally extending tip support section; and a distal tip section connected to said tip support section; said tip support section having a plurality of axially spaced apart transverse grooves defined in an outer surface thereof along a first length and a tapered diameter along a second length between said plurality of spaced apart grooves and said distal tip section for enhancing flexibility while resisting buckling to thereby facilitate placing the guidewire within a patient, said tip support section having a plurality of axially spaced apart longitudinally extending cylindrical outer surface portions between adjacent transverse grooves of constant and uniform circular cross-section and collectively defining an imaginary circular cylinder of constant and uniform diameter, each of said transverse grooves having a pair of opposing outer edges, adjacent respective cylindrical outer surface portions, being rounded over to thereby facilitate positioning of said tip support section within a catheter.

11. A guidewire according to claim 10 wherein elongate flexible body is a unitary body of material.

12. A guidewire according to claim 10 wherein said guidewire further comprises a longitudinally extending main section connected to said tip support section opposite said distal tip section, wherein said main section has a circular cross-sectional shape of predetermined diameter, and wherein the imaginary cylinder defined by outer surface portions of said tip support section has a diameter equal to the predetermined diameter of said main section.

13. A guidewire according to claim 10 wherein said series of axially spaced apart transverse grooves are equally axially spaced apart transverse grooves which extend circumferentially around the outer surface of said tip support section.

14. A guidewire according to claim 10 wherein said tip support section has a length in a range of about 5 to 15 inches.

15. A guidewire according to claim 10 wherein said elongate unitary body is a metal wire; and wherein said distal tip section comprises a flattened portion of said metal wire and a wound coil surrounding said flattened portion so that said distal tip section is bendable and shape-retaining.

16. A combination of a catheter and a flexible guidewire positioned within the catheter for placing the catheter within a patient, said guidewire comprising:

an elongate flexible unitary body defining a longitudinally extending tip support section, said tip support section having a plurality of axially spaced apart transverse grooves defined in an outer surface thereof for enhancing flexibility while resisting buckling to thereby facilitate placing the catheter within a patient, said tip support section having a plurality of axially spaced apart longitudinally extending cylindrical outer surface portions between adjacent transverse grooves of constant and uniform circular cross-section and collectively defining an imaginary circular cylinder of constant and uniform diameter, each of said transverse grooves having a pair of opposing outer edges, adjacent respective cylindrical outer surface portions, being rounded over to thereby facilitate positioning of said tip support section within a catheter; and a distal tip section connected to said tip support section.

17. A guidewire according to claim 16 wherein said tip support section further comprises a tapered diameter portion extending longitudinally between said plurality of spaced apart grooves and said distal tip section.

18. A guidewire according to claim 16 wherein said guidewire further comprises a longitudinally extending main section connected to said tip support section opposite said distal tip section, wherein said main section has a circular cross-sectional shape of predetermined diameter, and wherein the imaginary cylinder defined by outer surface portions of said tip support section has a diameter equal to the predetermined diameter of said main section.

19. A guidewire according to claim 16 wherein said series of axially spaced apart transverse grooves are equally axially spaced apart transverse grooves which extend circumferentially around the outer surface of said tip support section.

20. A guidewire according to claim 16 wherein said tip support section has a length in a range of about 5 to 15 inches.

21. A guidewire according to claim 16 wherein said elongate flexible unitary body is a metal wire; and wherein said distal tip section comprises a flattened portion of said metal wire and a wound coil surrounding said flattened portion so that said distal tip section is bendable and shape-retaining.

22. A flexible guidewire for use in placing a catheter within a patient, said guidewire comprising:

an elongate flexible unitary body defining a longitudinally extending tip support section, said tip support section having a plurality of axially spaced apart transverse grooves defined in an outer surface thereof for enhancing flexibility while resisting buckling to thereby facilitate placing the guidewire within a patient, said tip support section having a plurality of axially spaced apart longitudinally extending cylindrical outer surface portions between adjacent transverse grooves of constant and uniform circular cross-section and collectively defining an imaginary circular cylinder of constant and uniform diameter, each of said transverse grooves having a pair of opposing outer edges, adjacent respective cylindrical outer surface portions, being rounded over to thereby facilitate positioning of said tip support section within a catheter.

23. A guidewire according to claim 22 further comprising a distal tip section connected to said tip support section, and wherein said tip support section further comprises a tapered diameter portion extending longitudinally between said plurality of spaced apart grooves and said distal tip section.

24. A flexible guidewire for use in placing a catheter within a patient, said guidewire comprising:

an elongate flexible body defining a longitudinally extending tip support section, said tip support section comprising groove means defined in an outer surface thereof for enhancing flexibility while resisting buckling to thereby facilitate placing the guidewire within a patient, said groove means comprising a plurality of axially spaced apart transverse grooves defined in an outer surface of said tip support section, said tip support section having a plurality of axially spaced apart longitudinally extending cylindrical outer surfaces portions between adjacent transverse grooves of constant and uniform circular cross-section and collectively defining an imaginary circular cylinder of constant and uniform diameter, each of said transverse grooves having a pair of opposing outer edges, adjacent respective cylindrical outer surface portions, being rounded over to thereby facilitate positioning of said tip support section within a catheter; and a distal tip section connected to said tip support section, said distal tip section comprising a portion of said elongate flexible body and a wound coil surrounding same so that said distal tip section is bendable and shape-retaining.

25. A guidewire according to claim 24 wherein said tip support section further comprises a tapered diameter portion extending longitudinally between said plurality of spaced apart grooves and said distal tip section.

26. A guidewire according to claim 24 wherein said elongate flexible body is a metal wire; and wherein said distal tip section comprises a flattened portion of said metal wire.

27. A method for forming a flexible guidewire for placing a catheter within a patient, the method comprising the steps of:

providing an elongate flexible unitary body defining a tip support section of the guidewire; and forming a plurality of axially spaced apart transverse grooves in an outer surface of the tip support section so that the tip support section has a plurality of axially spaced apart longitudinally extending cylindrical outer surface portions between adjacent transverse grooves of constant and uniform circular cross-section and collectively defining an imaginary cylinder of constant and uniform diameter for enhancing flexibility while resisting buckling to thereby facilitate placing the guidewire within a patient; and rounding over each pair of opposing outer edges of the plurality of transverse grooves, adjacent respective cylindrical outer surface portions, to thereby facilitate positioning of said tip support section within a catheter.

28. A method according to claim 27 further comprising the step of forming a bendable shape-retaining distal tip section adjacent the tip support section.

29. A method according to claim 28 wherein the step of forming the distal tip section comprises the steps of flattening a portion of the elongate flexible unitary body and covering same with a wound coil.

30. A method according to claim 28 further comprising the step of forming a tapered diameter section along the elongate flexible unitary body between the grooved portion of the tip support section and the distal tip section.

31. A method according to claim 27 wherein the step of forming a plurality of axially spaced apart transverse grooves comprises the step of forming a plurality of axially spaced apart grooves extending circumferentially around the outer surface of the tip support section.

32. A method according to claim 31 wherein the step of forming a plurality of spaced apart grooves comprises the step of forming a plurality of axially spaced apart grooves wherein each spaced apart groove has a width such that a ratio of the width to the spacing between adjacent grooves is in a range of about 0.10 to 10.

* * * * *